US007700807B2

(12) United States Patent
De Kleine et al.

(10) Patent No.: US 7,700,807 B2
(45) Date of Patent: Apr. 20, 2010

(54) PROCESS TO PREPARE ALKYL PHENYL PHOSPHATES

(75) Inventors: Lambertus A. De Kleine, Hengelo (NL); Juergen Klaus Seifert, Dessau (DE)

(73) Assignee: Supresta LLC, Ardsley, NY (US)

( * ) Notice: Subject to any disclaimer, the term of this patent is extended or adjusted under 35 U.S.C. 154(b) by 212 days.

(21) Appl. No.: 10/582,916

(22) PCT Filed: Oct. 21, 2004

(86) PCT No.: PCT/EP2004/052615

§ 371 (c)(1),
(2), (4) Date: Mar. 7, 2007

(87) PCT Pub. No.: WO2005/040177

PCT Pub. Date: May 6, 2005

(65) Prior Publication Data

US 2007/0270616 A1 Nov. 22, 2007

(30) Foreign Application Priority Data

Oct. 24, 2003 (EP) .................................. 03078364

(51) Int. Cl.
*C07F 9/02* (2006.01)

(52) U.S. Cl. .......................................................... 568/8

(58) Field of Classification Search ...................... 568/8
See application file for complete search history.

(56) References Cited

U.S. PATENT DOCUMENTS

| | | | | |
|---|---|---|---|---|
| 2,759,962 | A * | 8/1956 | Zenftman et. al. | 558/210 |
| 3,931,367 | A * | 1/1976 | Giolito et al. | 558/150 |
| 4,034,023 | A * | 7/1977 | Hardy et al. | 558/92 |
| 6,075,158 | A * | 6/2000 | Hill | 558/118 |
| 7,166,736 | B2 * | 1/2007 | Bright et al. | 558/70 |

FOREIGN PATENT DOCUMENTS

| | | |
|---|---|---|
| DE | 566514 | 12/1932 |
| DE | 1140920 | 12/1962 |
| WO | 96/05208 | 2/1996 |

* cited by examiner

*Primary Examiner*—Jafar Parsa
*Assistant Examiner*—Chukwuma O Nwaonicha

(57) ABSTRACT

A process is provided for reacting dichloromonophenyl phosphate and monochlorodiphenyl phosphate with aliphatic alcohol in the presence of a Lewis acid catalyst and absence of solvent, at a temperature above 60 to 200° C. and pressure of 0.001 to 1.1 bara, and sparging the reaction mixture with an inert carrier gas if the pressure is above 0.67 bars. Mixtures of monoalkyl biphenyl phosphates and dialkyl monophenyl phosphates and use of such mixtures as a plasticizer and/or flame retardant, are also provided.

17 Claims, No Drawings

PROCESS TO PREPARE ALKYL PHENYL PHOSPHATES

BACKGROUND OF THE INVENTION;

The present invention relates to a process to prepare alkyl phenyl phosphates from a mixture comprising monophenyl dichlorophosphate and diphenyl mono-chlorophosphate.

A process to prepare alkyl phenyl phosphates is described in U.S. Pat. No. 2,504,121. Monalkyl diaryl phosphate esters are prepared by reaction of an alkylchloro-phosphate and a phenolate compound. The alkylchlorophosphate is formed in a preceding step by reaction of phosphorus oxychloride and an alcohol. The phenolate compound is formed by reaction of phenol compound and a base. U.S. Pat. No. 2,504,121 teach that the reaction of a phenyl chlorophosphate compound with an aliphatic alcohol is objectionable, as the reaction is difficult to control and excessive quantities of triaryl phosphates are formed.

A process to prepare alkyl phenyl phosphates is also known from U.S. Pat. No. 6,299,887. In this publication an alkyl phenyl phosphate, more specifically (2-heptylundecyl)diphenyl phosphate, is synthesised by reaction of diphenyl phosphoryl chloride with 2-heptylundecyl alcohol in the presence of a triethyl-amine catalyst and an acid amine scavenger. Similarly, U.S. Pat. No. 6,136,997 relates to undesired processes starting from diphenyl phosphoryl chloride. It is not disclosed or suggested to start with a mixture of monoalkyl phenyl phosphate and dialkyl monophenyl phosphate.

SUMMARY OF THE INVENTION

The present invention aims to provide an alternative and simplified process for the preparation of mixtures of monoalkyl diaryl phosphate esters and dialkyl monoaryl phosphate esters wherein no HCl scavengers need to be used, while at the same time it results in a very pure product and a low level of triphenyl phosphate. Further, the process according to the invention is improved in that it can be carried out in the absence of solvent, and strong bases which is advantageous. Moreover, the invention aims to provide a process wherein only a slight molar excess or no excess at all (compared to stoichiometric) of alcohol is required to substitute the chloro groups of the monophenyl dichlorophosphate and/or diphenyl monochlorophosphate compounds, while at the same time a good overall yield of alkyl phenyl phosphate is acquired. Also, it is a goal to make the HCl which is formed in the reaction available in a form which allows further use without extensive purification steps. Further, the invention aims to provide an economical process that gives a low amount of chlorinated by-products and a low acid value. Because of the low amount of by-products, less waste is formed, with the associated environmental benefits.

It was surprisingly found that most, if not all, of these goals can be reached by selecting the proper process conditions. Accordingly, the present invention relates to specific processes wherein a dichloromonophenyl phosphate and monochlorodiphenyl phosphate is reacted with an aliphatic alcohol, in the presence of a Lewis acid catalyst, in the absence of solvent at a temperature of above 60 to 200° C., and a pressure of 0.001 to 1.1 bara (absolute pressure, atmospheric pressure being 1 bara), provided that the reaction mixture is sparged with an inert carrier gas, such as nitrogen gas, if the pressure is above 0.67 bara.

Further, the process is performed at low $H_2O$ levels, preferably free of water, such that any HCl generated is efficiently (>90%, preferably >95%, most preferably >99%) removed as HCl gas by means of the vacuum and/or the sparging gas, with high yields at low catalyst concentrations. In a more preferred embodiment, the present process to prepare alkyl phenyl phosphates is running at a pressure below atmospheric pressure, preferably a pressure of at least 0.001 bara, preferably at least 0.25 bara, more preferably at least 0.3 bara and most preferably at least 0.35 bara and at most 0.99 bara, preferably at most 0.98 bara, more preferably at most 0.95 bar, and most preferably at most 0.9 bara, because it is economically more attractive. At all these pressures, the use of a sparging gas can be beneficial. At pressures above 0.67 bara it is necessary to use a carrier gas to efficiently remove the HCl that is formed. If the reaction mixture is sparged with a carrier, it is preferably done with a sparge flow of 0.1 to 100 $m^3/h$, preferably of 0.2 to 75 $m^3/h$, more preferably of 0.4 to 50 $m^3/h$ per $m^3$ of reaction volume. Any dry and inert (to the reaction mixture) gas can be used such as air, nitrogen, argon, helium, and the like, or mixtures thereof. The dew point of the sparging gas is preferably below 0° C., more preferably below −20° C. and most preferably below −70° C.

In another preferred embodiment, a pressure of at least 0.001, preferably at least 0.002, more preferably at least 0.003 bara and at most 0.065, more preferably below 0.06, and most preferably below 0.05 bara is applied in the process. At such low pressures the use of a sparging/carrier gas is not require to achieve the desired process performance.

It is noted the EP-A-0 775 147 describes a process to prepare a mixture of a monoalkyl diphenyl phosphate and a dialkyl monophenyl phosphate. More specifically, the synthesis of a mixture of isododecyl diphenyl phosphate and diisododecyl monophenyl phosphate by transesterification of triphenyl phosphate with isododecyl alcohol and the synthesis of a mixture of 2-ethylhexyl diphenyl phosphate and di-2-ethylhexyl monophenyl phosphate by transesterification of triphenyl phosphate with 2-ethylhexyl alcohol are described. However, this process results in a mixture having a high residual amount of triphenyl phosphate, which for various reasons (e.g. from a product performance or ecological point of view) is disadvantageous. Further, this process is hard to control and not economical. Moreover, in this process (contaminated) phenol is formed as a by-product, which is disadvantageous.

Further, it should be noted that in U.S. Pat. No. 6,242,631 a mixture of monophenyl dichlorophosphate and diphenyl monochlorophosphate is used as a starting mixture to prepare a mixture of substituted phenyl-phenyl phosphates. For example, a mixture of monophenyl dichlorophosphate and diphenyl monochlorophosphate reacts with phenyl alcohol in the presence of magnesium chloride and in the absence of solvent at a temperature of 145° C. and atmospheric pressure. It is also noted that in U.S. Pat. No. 5,457,221 a mixture of monophenyl dichlorophosphate and diphenyl monochlorophosphate is used as a starting mixture to prepare polyhydrocarbylene aryl phosphate compositions. For example, a mixture of monophenyl dichlorophosphate and diphenyl monochlorophosphate reacts with an aromatic diol in the presence of magnesium chloride and in the absence of solvent at a temperature of 150° C. and atmospheric pressure. However, these two patents do not read on the type of phosphate derivatives of the present invention and the benefits that the products of the invention have over the products mentioned therein, and the patents do not disclose or suggest to react a mixture of monophenyl dichlorophosphate and diphenyl monochlorophosphate with a non-phenolic alcohol.

It is noted that also U.S. Pat. No. 4,034,023 discloses a process to make a mixture-of alkyl phenyl phosphates. However, in this process the HCl is being complexed to the alcohol which is undesired. Also, the resulting mixture has a too low content of alkyl diphenyl phosphate, making the mixture unsuitable for many applications. In this description "in the absence of solvent" or "solvent-free" means that less than 5 wt % solvent is used, preferably less than 3 wt %, more preferably less than 2 wt %, even more preferably less than 1 wt %, based on the weight of the total reaction mixture.

It is further noted that in this description the term bar is used for the absolute pressure in bar (bara).

By the term phenyl phosphate is meant a phosphate esterified with a phenyl group and/or a substituted phenyl group such as a phenyl group substituted with a $C_1$-$C_6$ alkyl group and/or a $C_1$-$C_6$ alkoxy group. Preferably, the phenyl group is an unsubstituted phenyl group.

The present invention further relates to a two-step process wherein in a first step a mixture of monophenyl dichlorophosphate and diphenyl monochloro-phosphate is prepared. In this first step phosphorus oxychloride is reacted with phenol and the pressure being atmospheric pressure or higher, and the temperature preferably being between 60 and 200° C. More preferably, the pressure is between 1 and 1.5 bar and the temperature between 95 and 160° C. This first reaction step can be carried out in the desired way without the addition of any catalyst at all. In some cases, however, it may be advantageous to carry the reaction out in the presence of a suited catalyst, such as e.g. a Lewis acid catalyst.

In the second step the dichloromonophenyl phosphate and monochlorodiphenyl phosphate mixture of the first step is reacted with an aliphatic alcohol in the presence of a Lewis acid catalyst and in the absence of solvent at a temperature of above 60 to 200° C. and a pressure of 0.001 to 1.1 bara (absolute pressure, atmospheric pressure being 1 bara), provided that the reaction mixture is sparged with an inert carrier gas, such as nitrogen gas, if the pressure is above 0.67 bara.

DESCRIPTION OF THE PREFERRED EMBODIMENTS

In an especially preferred embodiment of the two-step process, (all) Lewis acid catalyst is added in the first step of the process and in the second step of the process no additional Lewis acid catalyst (or any other additional type of catalyst) is added. In another embodiment of the invention at least part of the monophenyl dichlorophosphate is removed from the reaction mixture from the first reaction step by a distillation or rectification step.

The mass ratio of phosphorus oxychloride to phenol in the first step preferably is 1 to 2, more preferably 1 to 1.5, even more preferably 1.05 to 1.4, most preferably 1.1 to 1.3.

In a preferred embodiment of the two-step process, monophenyl dichloro-phosphate resulting from the first step is (partly) recycled in the process and again reacted (in the first step) with phenol, such that the ratio of diphenyl monochlorophosphate to monophenyl dichlorophosphate in the mixture, that subsequently reacts in step 2 with the aliphatic alcohol, increases. In this way the ratio of diphenyl monoalkyl phosphate to monophenyl dialkyl phosphate and the content of triphenyl phosphate in the resulting mixture can be tailored to the actual requirements.

In another preferred embodiment, the two-step process, optionally including the recycling of monophenyl dichlorophosphate, is performed continuously.

In a further preferred embodiment, an additional distillation or rectification step is performed with this reaction mixture of monophenyl dichlorophosphate, diphenyl monochlorophosphate and (if present) triphenylphosphate to further reduce the content of monophenyl dichlorophosphate as desired in the resulting mixture.

The Lewis acid that can be used in the processes according to the invention includes any Lewis acid capable of promoting the reaction as known to the person skilled in the art and includes the halides of Group II and Group III metals. As examples may serve $AlCl_3$, $TiCl_4$, $ZnCl_2$, $CaCl_2$, $MgCl_2$ (or their respective bromides or Iodides), and MgO. Preferred Lewis acids are aluminum chloride ($AlCl_3$) and magnesium chloride ($MgCl_2$). Most preferred is the Lewis acid magnesium chloride. The amount of Lewis acid that is used is generally above 10 ppm, based on the total amount of phenyl chlorophosphate starting materials, preferably the amount of Lewis acid catalyst is above 100 ppm, more preferably above 150 ppm, even more preferably above 200 ppm, most preferably above 800 ppm. The amount of Lewis acid generally is below 3,000 ppm, based on the total amount of phenyl chlorophosphate starting materials, preferably the amount of Lewis acid catalyst is below 2,000 ppm, more preferably below 1,750 ppm, even more preferably below 1,500 ppm, most preferably below 1,000 ppm. In the embodiment relating to a two-step process wherein the Lewis acid is added completely at the first step, the amount of Lewis acid is in the same ranges as given above, based on phenyl chlorophosphate products resulting from the first step.

The aliphatic alcohol used in the processes of the invention can be any alcohol known to the person skilled in the art wherein a hydroxyl group is linked to a $C_1$-$C_{16}$ hydrocarbon group. Preferably the hydrocarbon is an alkyl group. The hydrocarbon group can be branched or linear, cyclic or noncyclic, can be a completely saturated or partly unsaturated hydrocarbon group, and can comprise substituents such as aryl groups and substituents that contain heteroatoms such as halogens; oxygen, sulphur, and nitrogen, which substituents may themselves be substituted with further substituents. More preferred aliphatic alcohols for use in the processes of the invention include saturated $C_1$-$C_{16}$, more preferably $C_1$-$C_{12}$, alcohols. Examples of most preferred aliphatic alcohols are n-butanol, i-butanol, 2-ethylhexanol, n-octanol, i-octanol, n-decanol, i-decanol, n-dodecanol, i-dodecanol, and cyclohexanol.

The molar ratio between the hydroxyl groups in the aliphatic alcohol and the chloro groups in the monochlorodiphenyl phosphate and/or dichloromonophenyl phosphate in any of the processes of the invention preferably is 1:1 to 1.5:1, more preferably 1:1 to 1.3:1, even more preferably 1:1 to 1.2:1, and most preferably 1:1 to 1.1:1. It is to be noted that at the reaction temperature of aliphatic alcohol and phenyl chlorophosphates the alcohol is typically refluxing. In order to prevent the formation of by-products in the process, it is preferred to dose the aliphatic alcohol into the reaction mixture with a low HCl level. When operated under such conditions, there will be hardly any reaction/scavenging of HCl by the alcohol. This has the added benefit that all HCl that is formed can be easily retrieved from the process and may even be sold.

The processes according to the invention may optionally comprise an additional purification step. Such purification step may include washing the product, vacuum distillation or wiped film evaporation. Preferably, the product is purified by washing. More preferably, washing is done in a number of steps using water and/or aqueous solutions with up to 10 wt % of a base or acid, even more preferably 0.2 to 5 wt %, most preferably 0.5 to 2 wt % of a base or acid. The base or acid can be any base or acid known by the person skilled in the art to be soluble in water and suitable for washing a product. Suitable acids include HCl, $H_2SO_4$, $H_3PO_4$, $CH_3COOH$, HOOC- COOH. Particular preference is given to HOOCCOOH, in particular in a concentration range from 0.5 to 10% in water. Suitable bases for the alkaline wash include conventional basic salts such as NaOH, $Na_2CO_3$, $NaHCO_3$, sodium acetate, and corresponding potassium salts. Among these the sodium salts are more preferred, in particular NaOH in a concentration range from 0.5 to 10% in water.

The processes according to the invention may be a continuous, semi-continuous or batch process. Preferably it is not a batch process. Most preferably it is a continuous process.

A separate embodiment of the present invention relates to the alkyl phenyl phosphates and alkyl phenyl phosphate mixtures obtainable by the processes according to the current invention. These alkyl phenyl phosphates and alkyl phenyl phosphate mixtures have good characteristics as plasticisers and are further suitable for use as flame retardants and lubricants.

The alkyl phenyl phosphate products formed from any of the processes according to the invention were found to have good characteristics as plasticizers, lubricants and/or flame retardants, particularly as plasticizers, and/or flame retardants. More preferably they are used as a plasticizer, most preferably as a plasticizer for PVC. Accordingly the invention further relates to alkyl phenyl phosphate mixtures obtainable by processes according to the invention and the use thereof, preferably as a plasticizer. It is noted that substitutes-phenyl phenyl phosphates and the reaction products of aromatic alcohol-derived phenyl phosphates are not suitable for this purpose.

In a preferred process a mixture containing a larger amount of diphenyl monoalkyl phosphate and a smaller amount of monophenyl dialkyl phosphate is produced. More specifically, a preferred mixture contains 25 to 99.9 weight %, preferably 35 to 99 weight %, more preferably 40 to 98 weight %, even more preferably 45 to 95 weight % diphenyl monoalkyl phosphate, based on the total amount of phenyl alkyl phosphates. The alkyl phenyl phosphate mixtures in general have a desired ratio of diphenyl monoalkyl phosphate to monophenyl dialkyl phosphate of 1:1 to 100:1, preferably 2:1 to 90:1, more preferably 5:1 to 80:1, even more preferably 10:1 to 70:1, most preferably 15:1 to 50:1. Preferably, the mixture contains less than 10 wt % of triphenyl phosphate is present, based on the total amount of phenyl phosphate compounds, more preferably less than 5 wt %, even more preferably less than 4 wt %, most preferably less than 3 wt %. Accordingly, the processes according to the invention are preferably those wherein such mixtures are produced.

The present invention is further illustrated by the following Examples

EXAMPLES

Laboratory scale experiments were done in a 2-litre jacketed glass reactor equipped with a 4-blade propeller agitator, a condenser, and a sub-surface liquid addition capability. A Vacuubrand diaphragm vacuum pump was used to control the vacuum in the reactor. A caustic scrubber was used to scrub hydrogen chloride formed in the reaction.

Scale-up experiments were done in 400- and 7,500-litre glass-lined jacketed reactors equipped with an agitator, a condenser, and a sub-surface liquid addition capability. Effluent gas from the reactor was scrubbed with water. Vacuum in the reactors was controlled by using either a liquid-ring vacuum pump or steam jet ejectors.

Purification of the crude reaction mixture was done using sequential washing in the same reactor vessel. Aqueous solutions were added to the product at 60° C. and agitated for about 30 minutes. The mixture was then allowed to phase separate for about 30 min. After the final washing step, the product was dehydrated under vacuum to remove water carried over from the washing process. The dehydrated product was filtered using standard filtration equipment. In commercial application steam and/or $N_2$ sparging could be used to further purify the dehydrated product and/or fractional distillation stripping could be used to further reduce the residual alcohol and chloride contents.

The reaction feeds, crude reaction product, and finished product were analysed for their composition by gas chromatography using a FID detector. In addition, wet analysis and potentiometric titration were used to measure acid phosphate composition, dissolved HCl, and acid numbers in the crude reaction product and finished product samples.

Examples 1 to 6

To the phosphochloridate mixture (6.4 wt% phenyl dichioridophosphate (MPCP), 89.7 wt % diphenyl chloridophosphate (DPCP), 3.9% triphenyl phosphate (TPP), and about 0.1 wt % $MgCl_2$) 2-ethylhexanol was added via subsurface addition at reaction conditions. Table 1 summarises the reaction conditions and the crude product compositions for both the laboratory scale and pilot scale experiments. Acceptable product quality is achieved under all reaction conditions summarised in Table 1. Efficient HCl removal is required for minimising the by-product formation. In these examples vacuum is the key method for HCl removal.

Examples 7 and 8

The crude from the reaction mixture of Example 1 and Example 5 was washed using the following sequence:

1% oxalic acid solution wash.

1% NaOH solution wash.

Water wash.

Water wash.

The composition of the product after purification by washing is summarised in Table 2.

TABLE 1

Summary of experimental conditions and crude reaction product compositions for Examples 1 through 6.

| Example | Reaction Scale [Litres] | Reaction Feed Amounts [kg] DPCP mix[1] | Reaction Feed Amounts [kg] 2-EH[2] | Reaction Conditions T [° C.] | Reaction Conditions P [mmHg] | Reaction Conditions Addition Time [Hrs] | Reaction Conditions Post Addition Reaction [Hrs] | Crude Reaction Product Composition 2-EHCl[3] [wt %] | 2-EH[2] [wt %] | TPP [wt %] | 2-EHDPPh[4] [wt %] | 2-EHPPh[5] [wt %] | DPAP[6] [wt %] | Acid Number [mg KOH/g] |
|---|---|---|---|---|---|---|---|---|---|---|---|---|---|---|
| 1 | 2 | 1 | 0.528 | 120 | 150 | 1.5 | 4 | 1.6 | ND | 3.2 | 81.4 | 9.6 | 4.2 | 7.6 |
| 2 | 2 | 1 | 0.528 | 120 | 150 | 1.5 | 4 | 1.5 | 0.5 | 3.3 | 81.3 | 9.7 | 3.7 | 7.3 |
| 3 | 2 | 0.500 | 0.264 | 120 | 150 | 3 | 4 | 1.2 | 0.8 | 3.3 | 81.4 | 9.7 | 3.7 | 7.9 |
| 4 | 2 | 0.500 | 0.264 | 120 | 50 | 1.5 | 4 | 0.7 | 0.4 | 3.3 | 84.1 | 10.0 | 1.5 | 2.9 |

TABLE 1-continued

Summary of experimental conditions and crude reaction product compositions for Examples 1 through 6.

| Example | Reaction Scale [Litres] | Reaction Feed Amounts [kg] DPCP mix[1] | 2-EH[2] | Reaction Conditions T [° C.] | P [mmHg] | Addition Time [Hrs] | Post Addition Reaction [Hrs] | Crude Reaction Product Composition 2-EHCl[3] [wt %] | 2-EH[2] [wt %] | TPP [wt %] | 2-EHDPPh[4] [wt %] | 2-EHPPh[5] [wt %] | DPAP[6] [wt %] | Acid Number [mg KOH/g] |
|---|---|---|---|---|---|---|---|---|---|---|---|---|---|---|
| 5 | 400 | 120.2 | 63.5 | 120 | 150 | 2 | 4 | 3.0 | ND | 3.4 | 81.0 | 9.8 | 2.2 | 6.6 |
| 6 | 400 | 228.6 | 118.1 | 120 | 50 | 3 | 4 | 1.3 | ND | 3.2 | 86.4 | 7.1 | 2.3 | 5.3 |

[1]DPCP mix - phosphochloridate mixture with the following composition - 6.4 wt % phenyl dichloridophosphate (MPCP), 89.7 wt % diphenyl chloridophosphate (DPCP), 3.9% triphenyl phosphate (TPP), and about 0.1 wt % $MgCl_2$.
[2]2-EH—2-ethylhexanol,
[3]2-EHCl—2-ethylhexylchloride,
[4]2-EHDPPh—2-ethylhexyldiphenyl phosphate,
[5]bis(2-ethyhexyl) phenyl phosphate,
[6]DPAP—diphenyl acid phosphate.

TABLE 2

Composition of product samples after purification (Examples 7 and 8).

| Example | Crude | Washing Conditions T [° C.] | Agitation Time [min] | Settling Time [min] | Product Composition after purification 2-EHCl[1] [wt %] | 2-EH[2] [wt %] | TPP | 2-EHDPPh[3] [wt %] | 2-EHPPh[4] [wt %] | DPAP[5] [wt %] | Acid Number [mg KOH/g] |
|---|---|---|---|---|---|---|---|---|---|---|---|
| 7 | From Example 1 | 60 | 30 | 30 | 1.2 | ND | 3.4 | 85.4 | 10.0 | ND | |
| 8 | From Example 2 | 60 | 30 | 30 | 1.1 | 0.5 | 3.4 | 85.0 | 10.1 | ND | |
| 9 | From Example 5 | 60 | 30 | 30 | 1.3 | 1.0 | 3.3 | 83.7 | 10.7 | ND | |

Composition of product samples after purification (Examples 7 and 8

Examples 9 through 12

To the phosphochloridate mixture (6.3 wt % phenyl dichloridophosphate (MPCP), 91.2 wt % diphenyl chloridophosphate (DPCP), 2.3% triphenyl phosphate (TPP), and 0.1 wt % $MgCl_2$) isodecyl alcohol (EXXAL-10) was added via subsurface addition at reaction conditions. The isodecyl alcohol used in these examples is comprised of mixed isomers. Table 3 summarises the reaction conditions and the crude product compositions for both the laboratory scale and pilot scale experiments. Acceptable product quality is achieved under all reaction conditions summarised in Table 3. Efficient HCl removal is required for minimising the by-product formation. In these examples vacuum is the key method for HCl removal.

Examples 13 and 14

In these examples the reaction between the phosphochloridate mixture and isodecyl alcohol was conducted in a batch fashion instead of the semi-batch operation. To the phosphochloridate mixture (401 gms) with the composition summarised in Examples 9 through 11 isodecylalcohol (253 gms) was added at room temperature. The mixture was brought to 100° C. and 100 mm Hg. The reaction was carried out for 4 hours and the crude was analysed. The crude composition is summarised in Table 4.

Examples 15 and 16

The crude product obtained from Example 10 and Example 12 was further purified by washing using the following sequence:

1% oxalic acid solution wash.
1% NaOH solution wash.
Water wash.
Water wash.

The composition of the purified product is summarised in Table 4.

Example 17

The purified product of Example 16 was further purified by steam stripping to remove excess alcohol and alkyl chloride. Steam was sparged into the reactor containing the product via a dip tube. Vacuum was maintained between 100 mm Hg and 10 mm Hg and the temperature was varied between 80° C. and 120° C. Although this experiment was conducted under non-optimised conditions, we were able to achieve significant reduction in the alcohol and chlorides from about 5.0 area% to about 0.6 area % under the experimental conditions explored. Although steam was used as the stripping agent in this example, any suitable stripping agent could be used to achieve the end result of reducing the alcohol and chloride contents.

TABLE 3

Summary of experimental conditions and crude reaction product compositions for Examples 9 through 12

| Example | Reaction Scale [Litres] | Reaction Feed Amounts [kg]: DPCP mix[1] | Reaction Feed Amounts [kg]: Isodecyl Alcohol[2] | Reaction Conditions: T [° C.] | Reaction Conditions: P [mmHg] | Reaction Conditions: Addition Time [Hrs] | Reaction Conditions: Post Addition Reaction [Hrs] | Crude Reaction Product Composition: Phenol [wt %] | Isodecyl Alcohol + Isodecyl Chloride[3] [wt %] | TPP [wt %] | IDPPh + IDPPh[3] [wt %] | DPAP[4] [wt %] | Acid Number [mg KOH/g] |
|---|---|---|---|---|---|---|---|---|---|---|---|---|---|
| 9 | 2 | 0.5[1] | 0.317 | 120 | 50 | 2 | 2 | ND | 5.6 | 1.5 | 87.1 | 6.3 | 14.0 |
| 10 | 2 | 0.401[1] | 0.264 | 100 | 50 | 3 | 4 | 0.19 | 3.95 | 1.5 | 90.45 | 3.7 | 8.4 |
| 11 | 2 | 0.432[1] | 0.284 | 90 | 50 | 2 | 5 | 0.17 | 2.7 | 1.5 | 94.6 | 2.8 | 6.2 |
| 12 | 7500 | 4493[2] | 2698 | 90 | 50 | 5 | 2 | 0.28 | 5.4 | 3.7 | 86.2 | 2.5 | 7.2 |

[1]DPCP Mix - 6.3 wt % phenyl dichloridophosphate (MPCP), 91.2 wt % diphenyl chloridophosphate (DPCP) and 2.3% triphenyl phosphate (TPP).
[2]DPCP Mix - 5.7 wt % MPCP, 86.2% DPCP and 6.8% TPP.
[3]Isodecyl Alcohol (EXXAL-10 obtained from Exxon Mobil) comprised of mixed isomers.
[4]GC method used in general did not differentiate between alkyl chlorides and isodecyl alcohol.
[5]IDDPPh—isodecyl diphenyl phosphate and IDPPh - bis(isodecyl) phenyl phosphate are reported as one value by the GC method used in the analysis.
[6]DPAP—diphenyl acid phosphate.

TABLE 4

Summary of experimental conditions and crude reaction product compositions for Examples 13 and 14

| Example | Reaction Scale [Litres] | Reaction Feed Amounts [kg]: DPCP mix[1] | Reaction Feed Amounts [kg]: Isodecyl Alcohol[2] | Reaction Conditions: T [° C.] | Reaction Conditions: P [mmHg] | Reaction Conditions: Addition Time [Hrs] | Reaction Conditions: Post Addition Reaction [Hrs] | Crude Reaction Product Composition: Phenol [wt %] | Isodecyl Alcohol + Isodecyl Chloride[3] [wt %] | TPP [wt %] | IDDPPh + IDPPh[4] [wt %] | DPAP[5] [wt %] | Acid Number [mg KOH/g] |
|---|---|---|---|---|---|---|---|---|---|---|---|---|---|
| 13 | 2 | 0.401 | 0.253 | 100 | 100 | Batch | 4 | ND | 1.8 | 1.5 | 90.5 | 1.6 | 3.9 |

[1]DPCP Mix - 6.3 wt % phenyl dichloridophosphate (MPCP), 91.2 wt % diphenyl chloridophosphate (DPCP), and 2.3% triphenyl phosphate (TPP).
[2]Isodecyl Alcohol (EXXAL-10 obtained from Exxon Mobil) comprised of mixed isomers.
[3]GC method used in general did not differentiate between alkyl chlorides and isodecyl alcohol.
[4]IDDPPh—isodecyl diphenyl phosphate and IDPPh - bis(isodecyl) phenyl phosphate are reported as one value by the GC method used in the analysis.
[5]DPAP—diphenyl acid phosphate.

TABLE 5

Composition of products of Examples 10 and 12 after purification by washing.

| Example | Crude | Washing Conditions: T [° C.] | Washing Conditions: Agitiation Time [min] | Washing Conditions: Settling Time [min] | Product Composition after purification: Phenol [wt %] | Isodecyl Alcohol + Isodecyl Chloride[3] [wt %] | TPP | IDDPPh + IDPPh[3] [wt %] | DPAP[5] [wt %] | Acid Number [mg KOH/g] |
|---|---|---|---|---|---|---|---|---|---|---|
| 14 | From Example 10 | 60 | 30 | 30 | 0.01 | 3.4 | 1.5 | 93.4 | ND | 0.016 |
| 15 | From Example 12 | 60 | 30 | 30 | 0.01 (GC area %) | 5.0 (GC area %) | 3.7 (GC area %) | 91.3 (GC area %) | ND | 0.01 |

The invention claimed is:

1. A process for producing alkylphenyl phosphates comprising the steps of reacting a dichloromonophenyl phosphate and monochlorodiphenyl phosphate with an aliphatic alcohol, in the presence of a Lewis acid catalyst, in the absence of solvent, at a temperature of above 60 to 200° C., and at a pressure of 0.001 to 1.1 bar absolute pressure (bara), and sparging the reaction mixture with an inert carrier gas in the event the pressure is above 0.67 bara.

2. The process according to claim 1 wherein the Lewis acid catalyst is magnesium chloride.

3. The process according to claim 1 wherein the removal of the by-product HCl is enhanced by sparging with a dry inert carrier gas.

4. The process according to claim 1 wherein the Lewis acid catalyst is used in an amount of 100 to 1.750 ppm, based on the total amount of phenyl chlorophosphate starting materials.

5. A process to prepare a mixture of monoalkyl diphenyl phosphates and dialkyl monophenyl phosphates wherein phosphorus oxychloride is reacted with phenol in a first step resulting in a mixture of diphenyl monochlorphosphates and monophenyl dichlorophosphates; and the mixture of diphenyl monochlorophosphates and monophenyl dichlorophosphates resulting from the first step is reacted with an aliphatic alcohol in a second step, in accordance with the process according to claim 1.

6. The process according to claim 5 wherein the Lewis acid catalyst is completely added to the first step of the process and in the second step of the process no additional Lewis acid catalyst is added.

7. The process according to claim 5 wherein at least part of the monophenyl dichlorophosphate from the first step is recycled, so that the alkyl diphenyl phosphate to dialkyl phenyl phosphate ratio of the product mixture of the second step is greater than the diphenyl chlorophosphate to monophenyl dichlorophosphate ratio resulting from the first reaction step without a recycle stream.

8. The process according to claim 5 wherein at least part of the monophenyl dichlorophosphate is removed from the reaction mixture from the first reaction step by a distillation or rectification step.

9. The process according to claim 1 comprising an additional purification step.

10. The process according to claim 1 that is a continuous, semi-continuous or batch process.

11. The process according to claim 2 wherein the removal of the by-product HCl is enhanced by sparging with a dry inert carrier gas and the Lewis acid catalyst is magnesium chloride.

12. The process according to claim 2 wherein the Lewis acid catalyst is used in an amount of 100 to 1.750 ppm, based on the total amount of phenyl chlorophosphate starting materials.

13. The process according to claim 3 wherein the Lewis acid catalyst is used in an amount of 100 to 1.750 ppm, based on the total amount of phenyl chiorophosphate starting materials.

14. The process according to claim 6 wherein at least part of the monophenyl dichlorophosphate from the first step is recycled, so that the alkyl diphenyl phosphate to dialkyl phenyl phosphate ratio of the product mixture of the second step is greater than the diphenyl chlorophosphate to monophenyl dichlorophosphate ratio resulting from the first reaction step without a recycle stream.

15. The process according to claim 6 wherein at least part of the monophenyl dichlorophosphate is removed from the reaction mixture from the first reaction step by a distillation or rectification step.

16. The process according to claim 7 wherein at least part of the monophenyl dichlorophosphate is removed from the reaction mixture from the first reaction step by a distillation or rectification step.

17. A process to prepare a mixture of monoalkyl diphenyl phosphates and dialkyl monophenyl phosphates wherein in a first step phosphorus oxychloride is reacted with phenol and in a second step in accordance with the process according to claim 2 the mixture of diphenyl monochlorophosphates and monophenyl dichlorophosphates resulting from the first step is reacted with an aliphatic alcohol.

* * * * *